(12) United States Patent
Drevik et al.

(10) Patent No.: US 7,919,169 B2
(45) Date of Patent: Apr. 5, 2011

(54) LAMINATE MADE OF FIBROUS LAYERS FOR USE IN ABSORBENT ARTICLES

(75) Inventors: Solgun Drevik, Mölnlycke (SE); John Kvamme, Askim (SE)

(73) Assignee: SCA Hygiene Products AB, Gothenburg (SE)

( * ) Notice: Subject to any disclaimer, the term of this patent is extended or adjusted under 35 U.S.C. 154(b) by 816 days.

(21) Appl. No.: 10/162,657

(22) Filed: Jun. 6, 2002

(65) Prior Publication Data

US 2003/0004482 A1  Jan. 2, 2003

Related U.S. Application Data

(60) Provisional application No. 60/296,485, filed on Jun. 8, 2001.

(51) Int. Cl.
 *B32B 3/10* (2006.01)
(52) U.S. Cl. ......... 428/138; 428/137; 604/367; 156/252
(58) Field of Classification Search .................. 604/369, 604/383, 367; 428/138, 198, 131, 134–137, 428/102–103, 141, 143; 156/252, 253, 291
See application file for complete search history.

(56) References Cited

U.S. PATENT DOCUMENTS

| | | | |
|---|---|---|---|
| 3,929,135 A | 12/1975 | Thompson | |
| 4,276,338 A * | 6/1981 | Ludwa et al. | 428/137 |
| 4,333,979 A | 6/1982 | Sciaraffa et al. | |
| 4,340,563 A | 7/1982 | Appel et al. | |
| 4,392,862 A | 7/1983 | Marsan et al. | |
| 4,397,644 A | 8/1983 | Matthews et al. | |
| 4,761,322 A | 8/1988 | Raley | |
| 4,798,603 A | 1/1989 | Meyer et al. | |
| 4,886,632 A | 12/1989 | Van Iten et al. | |
| 5,078,710 A * | 1/1992 | Suda et al. | 604/383 |
| 5,300,054 A * | 4/1994 | Feist et al. | 604/378 |
| 5,304,161 A * | 4/1994 | Noel et al. | 604/378 |
| 5,383,870 A * | 1/1995 | Takai et al. | 604/378 |
| 5,536,555 A * | 7/1996 | Zelazoski et al. | 428/138 |
| 5,603,707 A * | 2/1997 | Trombetta et al. | 604/383 |
| 5,613,960 A * | 3/1997 | Mizutani | 604/365 |
| 5,643,240 A * | 7/1997 | Jackson et al. | 604/378 |
| 5,667,619 A * | 9/1997 | Alikhan | 156/253 |
| 5,919,177 A * | 7/1999 | Georger et al. | 604/367 |

(Continued)

FOREIGN PATENT DOCUMENTS

EP  0 214 608 A2  3/1987

(Continued)

OTHER PUBLICATIONS

English translation of JP 10-272152 A to Mizutani, specification only.*

(Continued)

*Primary Examiner* — Melanie J Hand

(74) *Attorney, Agent, or Firm* — Buchanan Ingersoll & Rooney PC

(57) ABSTRACT

A laminate made of fibrous layers for use in absorbent articles, such as sanitary towels, nappies or the like. The laminate includes an outer layer (5) made of non-woven fabric, which is in contact with the wearer during use of the article, and an inner layer (6), which two layers are interconnected in a first bonding pattern consisting of separate bonding points (7).

18 Claims, 5 Drawing Sheets

U.S. PATENT DOCUMENTS

| | | | |
|---|---|---|---|
| 6,025,049 A | 2/2000 | Ouellette et al. | |
| 6,100,208 A * | 8/2000 | Brown et al. | 442/364 |
| 6,202,250 B1 * | 3/2001 | Kenmochi et al. | 15/231 |
| 6,274,218 B1 * | 8/2001 | Shimizu | 428/137 |

FOREIGN PATENT DOCUMENTS

| | | |
|---|---|---|
| EP | 0 235 309 B1 | 9/1987 |
| EP | 0 272 683 B1 | 6/1988 |
| EP | 0 409 535 B1 | 1/1991 |
| EP | 0 617 602 B1 | 10/1994 |
| EP | 1 153 737 A2 | 11/2001 |
| GB | 2 023 067 A | 12/1979 |
| GB | 2158721 A | 11/1985 |
| GB | 2158721 A * | 11/1985 |
| GB | 2 296 467 | 7/1996 |
| GB | 2 335 627 A | 9/1999 |
| JP | 60-259260 | 12/1985 |
| JP | 01256955 A | 10/1989 |
| JP | 05-247816 | 9/1993 |
| JP | 09-299402 | 11/1997 |
| JP | 10272152 A | 10/1998 |
| WO | WO 93/11725 | 6/1993 |
| WO | 97/40793 | 11/1997 |
| WO | WO 99/00082 | 1/1999 |

OTHER PUBLICATIONS

Notice of Opposition filed in a corresponding European application.
Notice of Reasons for Rejection mailed on Aug. 5, 2008 for Japanese Patent Application No. 2003-503433.

* cited by examiner

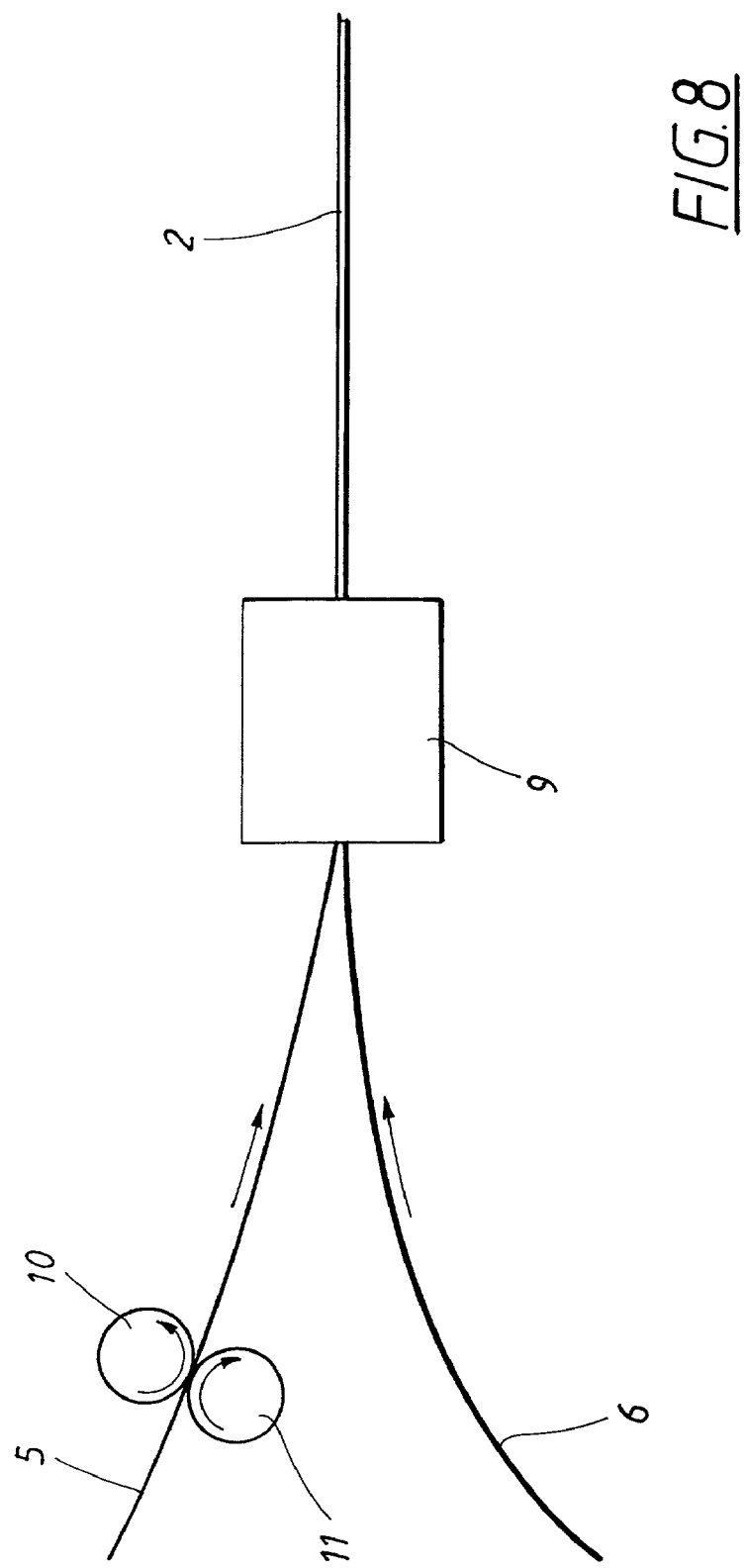

LAMINATE MADE OF FIBROUS LAYERS FOR USE IN ABSORBENT ARTICLES

CROSS-REFERENCE TO RELATED APPLICATIONS

The present application claims the priority of U.S. Provisional Application No. 60/296,485, filed in the United States on Jun. 8, 2001, the entire contents of which are hereby incorporated herein by reference.

BACKGROUND OF THE INVENTION

1. Technical Field

The present invention relates to a laminate made of fibrous layers for use in absorbent articles, such as sanitary towels, nappies or the like. The laminate includes an outer layer made of non-woven fabric, which is in contact with the wearer during use of the article, and an inner layer. The two layers may be interconnected in a first bonding pattern consisting of separate bonding points.

2. Background Art

Surface material for absorbent articles, such as sanitary towels, nappies or the like, means the layer which is located closest to the wearer and is in contact with the body of the wearer during use of the article. A surface material has many functional requirements, some of which are conflicting. The surface material is to feel soft and flexible to the wearer but must also be strong so as to withstand wear. It also should allow bodily fluid to rapidly pass through to the underlying absorbent body. The surface material also should prevent liquid which has been absorbed into the absorbent body from back-wetting the wearer.

Conventional surface materials in sanitary towels and nappies are non-woven fabrics, which are commercially available in a great many variants. Depending on the selection of fibers to be included in the non-woven material and the addition of any surface-active agents, such as wetting agents, the surface material is either hydrophobic or hydrophilic. Also, the liquid permeability can be controlled by varying the degree of hydrophilicity.

U.S. Pat. No. 4,333,979 describes a surface material made of non-woven fabric, which is formed from thermoplastic fibers bonded in a pattern, and is embossed so as to provide the surface material with increased thickness, softness, bulk and strength. The non-woven material consists of what is known as spunbond with separate melt-bonding points lying closely together in a pattern of separate embossings. The material in question is stated to be a very effective surface material in disposable absorbent products, such as nappies, sanitary towels and the like. The production process entails a material web being bonded by passing it through a roller nip between a heated roller pair, one of the rollers consisting of a pattern roller for forming said melt-bonding points. The production process also comprises permanent embossing of said embossing pattern in a roller nip formed by two heated, mutually matching embossing rollers. U.S. Pat. No. 4,333,979 therefore describes a material web consisting of a single layer which, as mentioned above, is double-embossed, on the one hand for bonding the web and on the other hand for creating thickness and bulk. The material has very good strength properties, but at the expense of softness and flexibility, which are worse owing to the double embossing.

Perforated non-woven fabric, that is to say fabric in which holes have been made so as to increase the liquid flow capacity, has also been available for a long time. An example of a perforated non-woven fabric is described in EP 235 309. The perforated non-woven material according to said publication consists of what is known as spunlace material with a high content of hydrophobic fibers. In a spunlace process, holes are formed in the material by means of water jets, which are sprayed against the material at high pressure. According to the publication, the spunlace material constitutes one of two layers forming the surface material and is intended to constitute the layer which is located closest to the wearer during use of the article. The aim is that the liquid be conducted through the holes and into the underlying layer. The spunlace material has a higher content of hydrophobic fibers than the underlying layer in the laminate. The fibers in the upper spunlace layer consist of 70% hydrophobic fibers and 30% hydrophilic fibers, while the underlying material layer consists of equal parts of hydrophobic and hydrophilic fibers. The underlying layer therefore has the capacity to drain liquid from the upper layer.

One problem with the material described in EP 235 309, however, is that holes which are formed by water jets are irregular in terms of both size and shape and have fibers which protrude from the edges of the holes and into the holes. These protruding fibers reduce the areas of the holes and capillary action draws the liquid into the material between the holes. The protruding fibre ends and the irregular shape and size of the holes considerably increase the risk of liquid remaining in the surface layer after wetting. Because even a small quantity of liquid on the surface material is sufficient to create a wet or soiled feeling for the wearer, this constitutes a major disadvantage of the material described in EP 235 309.

A similar material is described in EP 272 683 which also describes a surface material made of perforated non-woven fabric. In the disclosed fabric there are relatively loose fibers that are formed by perforating the non-woven material close to the holes that are intended to function as ducts for transporting liquid down to an underlying non-woven layer of what is known as the meltblown type.

As long as the fibers in the perforated layer are arranged in such a manner that they conduct liquid down to an underlying layer, the surface material functions properly. However, it is a well-known fact that a non-woven material consists of irregularly shaped fibers, which are difficult to arrange in any particular direction. This means that fibers which are intended to transport liquid down to an underlying ply will also spread liquid over the surface of the non-woven material. Therefore, some of the liquid will remain in the surface material after wetting, and the article with the surface material in question will feel wet and unpleasant against the body of the wearer.

Another problem with the surface material, as described above is the difficulty of obtaining a well-defined hole size. From EP 409 535, for example, it is well-known that the size of the holes in the perforated material is critical for obtaining optimum liquid-permeability. In the case of a non-woven material, which has some areas with a dense fibrous structure and other areas with a less dense structure, it is difficult to achieve a uniform hole size throughout the material. This is due to the fact that holes in denser fibrous areas are smaller because they are surrounded by more fibers.

Furthermore, perforated non-woven materials in such previously known surface materials have a relatively low tensile strength because the hole-manufacturing process weakens the material. As strength is important to minimize the risk of the material breaking during manufacture or use, the low tensile strength is of course a major problem.

In EP 214 608, the holes are made in the non-woven material by means of hot needles, which heat the material to a temperature just below the melting point of the material. The holes made in the material therefore have a condensed portion of the fibrous material around each hole. The problems of varying hole size and weakening of the material are thus eliminated to a certain extent. On the other hand, the problem of liquid being able to spread in the surface material and remain in the fibrous structure persists. The denser structure around the holes is also intended to draw liquid down into underlying layers, but there is an obvious risk of liquid remaining in the dense hydrophilic fibrous structure around the holes. There is also a risk of liquid spreading in the capillaries of the non-woven material and as the non-woven layer is in direct contact with the wearer, this represents a major disadvantage. Another problem is that, because portions around the holes are melted, the surface material is stiff and uncomfortable for the wearer compared with material without condensed and partly melted portions around the holes.

In WO 9740793, it has been proposed, in conjunction with the hole-punching, to seal the area around each hole so as to reduce liquid spread in the lateral direction, each hole being surrounded by an essentially liquidtight edge. In this case, however, the problem remains that the material may feel relatively stiff and uncomfortable to the wearer in comparison to a similar material without these seals around the holes.

In addition to the use of non-woven fabrics, good results have been obtained in recent years using perforated films, that is to say plastic films with a large number of small holes which are designed to allow liquid through in one direction and prevent or reduce flow in the opposite direction. Good results in terms of low back-wetting have been achieved using such materials. An early example of such a film material is described in U.S. Pat. No. 3,929,135. A later example of perforated plastic film is described in U.S. Pat. No. 6,025,049. One disadvantage of perforated plastic films is that they have a plastic feel, which troubles many wearers who want softer material with a fibrous and textile feel.

It has been difficult to provide all the desired properties of a surface material in a single layer, and it is therefore now common to have surface materials in the form of laminates consisting of two or more layers.

In order to achieve more rapid admission of liquid into the absorbent core of an absorbent product, and to create an insulating layer between the skin of the wearer and the absorbent core so as to prevent or at least reduce back-wetting, the surface material is now commonly combined with an underlying fibrous layer. An example of such a material combination is described in U.S. Pat. No. 4,761,322. Another example is described in U.S. Pat. No. 4,798,603, where a surface layer is supplemented by an underlying transport layer, said transport layer having a pore size which is smaller than the pore size in the surface layer. The latter publication states that such a material combination results in a higher liquid penetration rate and considerably lower back-wetting than a surface layer made only of, for example, spunbond. The surface layer in the absorbent article according to U.S. Pat. No. 4,798,603 can be perforated for better liquid penetration.

In the case of material combinations consisting of two or more layers closest to the wearer, it is important that the layers make good contact with one another so that insulating gaps do not occur between the outer and inner layers, because such a gap would constitute an impediment to liquid passing from one layer to the other. It is therefore necessary to bond the two layers together to form a laminate. This can be effected using bonding agent or by thermal bonding, for example ultrasonic bonding.

The bonding together is often carried out at separate places in a bonding pattern, on the one hand in order not to constitute an impediment to liquid flow, and on the other hand in order that the laminate is not too stiff. Compared with a laminate without a bonding pattern, however, the laminate is relatively stiff and feels hard and uncomfortable to a wearer.

OBJECTS AND SUMMARY

It is clear from the above that there is still a real need to improve laminates for use as surface layers on absorbent articles, such as sanitary towels, nappies or the like.

The invention relates, but is not limited, to laminates of the type mentioned in the introduction that are soft and comfortable for the wearer.

The laminate according to one embodiment of the invention contains holes that are made at least through the outer layer in a hole pattern of separate holes, the hole pattern having more holes per unit area than the number of bonding points per unit area.

One of the purposes of having the number of holes exceeding the bonding points between the outer and inner layers is to soften the material.

According to one embodiment of the invention, each of said holes is formed by arranging at least one slit through at least the outer layer and by pressing down an area thereby forming the respective hole opening from the outside of the layer.

In this particular embodiment, the fact that the material penetration for the holes consists of slits, fibers in at least the outer layer are cut through at each slit, resulting in this layer being more open, soft and flexible.

According to another embodiment of the present invention, each hole is formed by arranging two parallel slits delimiting the hole opening through at least the outer layer and by pressing down the rectangular area between the slits.

According to another embodiment of the invention, the outer layer consists of non-woven fabric with bonding points arranged in a second bonding pattern, where the second bonding pattern has fewer bonding points per unit area than the number of holes per unit area in said hole pattern.

According to another embodiment of the invention, the inner layer consists of a non-woven containing at least polyester fibers.

Further suitable embodiments emerge from the claims which follow.

BRIEF DESCRIPTION OF DRAWINGS

FIG. 8 shows diagrammatically a second method of manufacturing a laminate according to an embodiment of the invention.

DETAILED DESCRIPTION OF THE PREFERRED EMBODIMENTS

Figure 1:
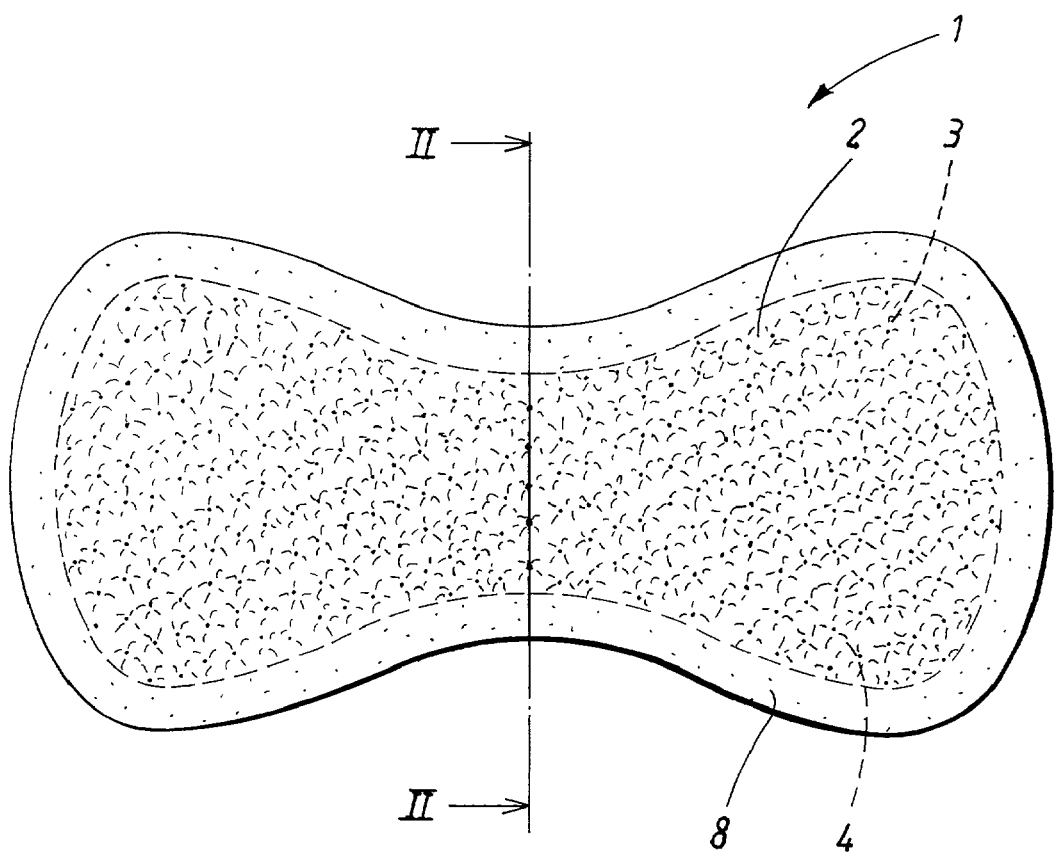
FIG. 1 shows diagrammatically a plan view of a sanitary towel with a laminate according to an embodiment of the invention.
Figure 2:
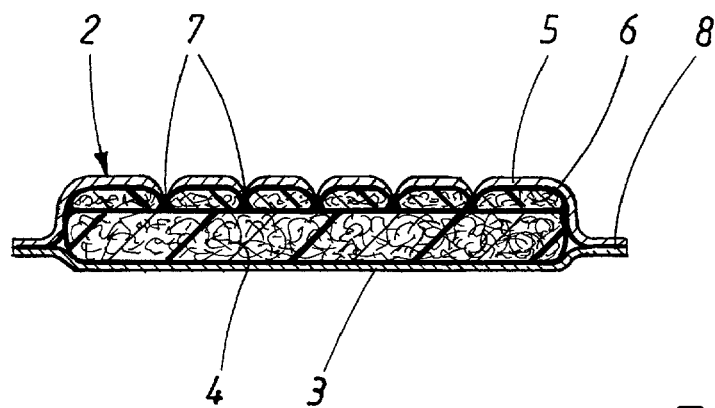
FIG. 2 shows a part of a cross section along the line II-II in FIG. 1.

According to one embodiment of the invention, FIGS. 1 and 2 show a sanitary towel 1 with a liquid-permeable laminate 2, and a liquid tight layer 3 in the form of a polyethylene film, and an absorbent body 4 arranged between the laminate and the liquid tight layer 3. The laminate 2 consists of an outer layer 5 made of non-woven fabric, which is in contact with the wearer during use of the sanitary towel, and an inner layer 6 made of a fibrous material. The two layers 5, 6 making up the laminate are interconnected in a first bonding pattern consisting of separate bonding points 7. This connection of the two layers making up the laminate will be described in greater detail below.

The expression bonding points is to be interpreted in such a way that the bonding points can have any shape and extent. For example, they can be in, but are not limited to, the form of a rhombus or a line.

The outer layer 5 in the laminate 2 extends a little way outside the inner layer 6 of the laminate, around the entire periphery of the sanitary towel, and is outside the absorbent body 4, and is connected to the liquid tight plastic layer 3 along an edge portion 8.

Figure 3:
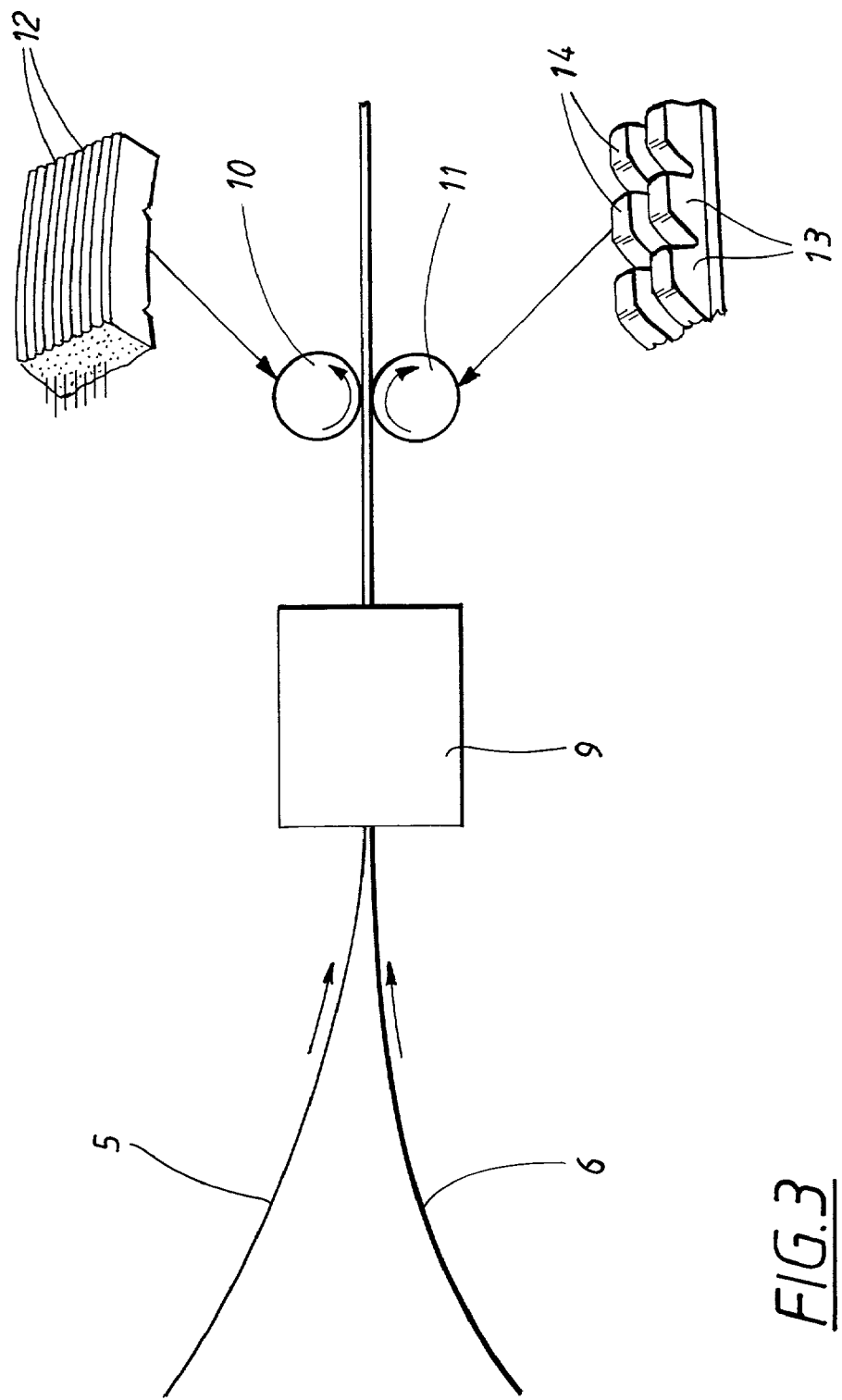
FIG. 3 shows diagrammatically a method of producing a laminate according to an embodiment of the invention.

FIG. 3 illustrates diagrammatically the production of a laminate 2 of FIGS. 1 and 2 according to an embodiment of the invention. The outer layer 5 in the laminate is fed, together with the inner fibrous layer 6, to an ultrasound unit 9, which can be of, but is not limited to, a conventional type and is not shown in greater detail. In the ultrasound unit, the two layers are bonded together in said bonding pattern consisting of separate bonding points.

The bonded-together laminate 2 is then fed to a perforating unit in the form of two rollers 10 and 11, which are intended to cut separated longitudinal incisions in the laminate for forming holes. As can be seen from an enlarged portion, the roller 10 has parallel knives 12 which run all the way around and can be arranged on the periphery of the roller by milling. The counter-roller 11 has peripheral teeth 13 which engage in the material and, with their upper portions 14, press the laminate against the knives 12. An example of a perforating arrangement of this type is described in greater detail in GB Patent No. 2 296 467.

Figure 4:
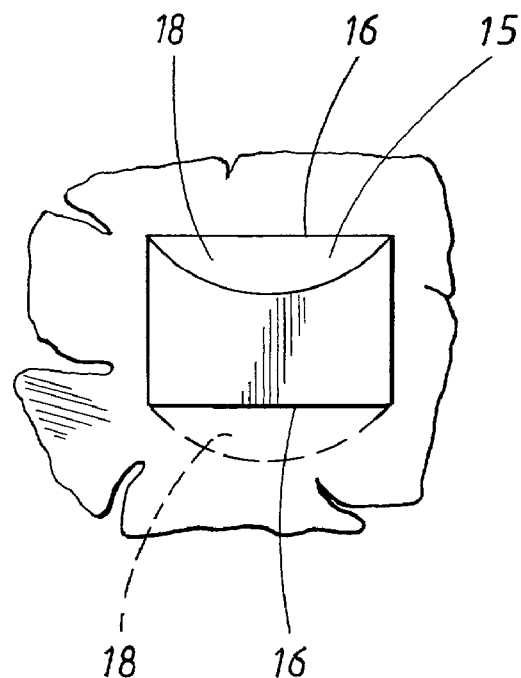
FIG. 4 shows an embodiment of a hole in the laminate according to an embodiment of the invention.

FIG. 4 shows diagrammatically a piece of the laminate to illustrate how holes in the laminate are formed after it has been perforated by the perforating rollers 10, 11 shown in FIG. 3. The hole, or rather the opening 15, in the laminate is delimited by two parallel incisions 16 cut by means of the knives 12. After the incisions 16 have been cut, a hammock-like portion is formed by pressing down the material between the slits 16 by means of the teeth 13 on the roller 11.

Figure 5:
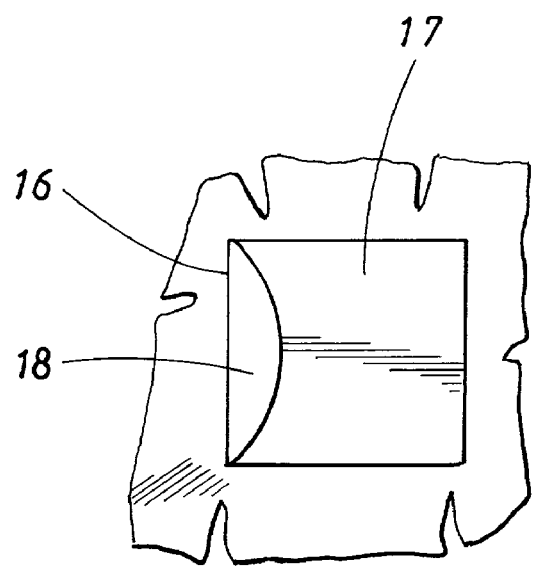
FIG. 5 shows a second embodiment of a hole in the laminate according to an embodiment of the invention.

According to another embodiment of the invention, FIG. 5 shows a hole which has been modified in relation to the hole according to FIG. 4 and in which there is only one slit 16 and an adjacent area 17 of the laminate has been pressed by means of teeth of a different shape to those shown in FIG. 3. The holes themselves, in the laminate according to the embodiments shown, are shaped like segments of a circle and have been designated by reference number 18 in FIGS. 4 and 5.

Figure 6:
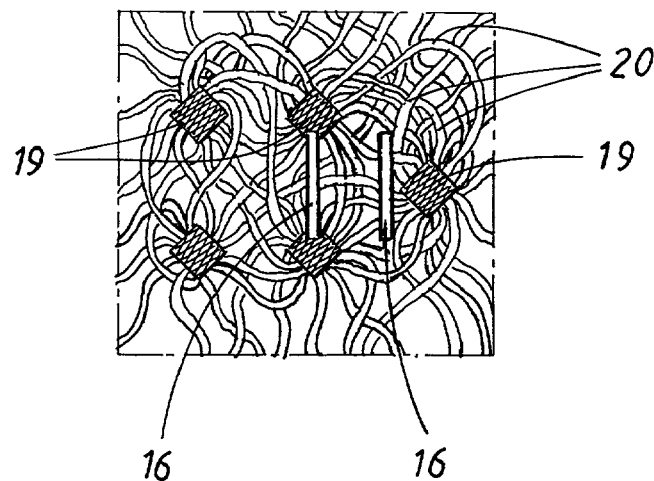
FIG. 6 shows diagrammatically a portion of an outer layer of the laminate according to an embodiment of the invention.

The outer layer in the laminate 2, according to an embodiment of the invention, can consist of, but is not limited to, a spunbond non-woven. FIG. 6 shows a portion of an outer layer 5 in the laminate according to an embodiment of the invention. According to this embodiment, the outer layer consists of a spunbond made of polypropylene fibers which are thermally bonded in a regular pattern of separate squares, which have been designated by reference number 19 in FIG. 6. FIG. 6 also shows the separated slits 16 described above. These are shown here in order to illustrate how in one embodiment of the invention slits are cut in the individual fibers 20 in the spunbond material. In FIG. 6, which is diagrammatic, only two of the slits have been drawn. Owing to the arrangement of the slits, the material is very open and also soft and flexible.

The thermal bonding can be brought about by, but is not limited to, means of ultrasound. The pattern does not of course have to consist of a regular pattern of separate points, and other patterns and shapes are possible.

Figure 7:
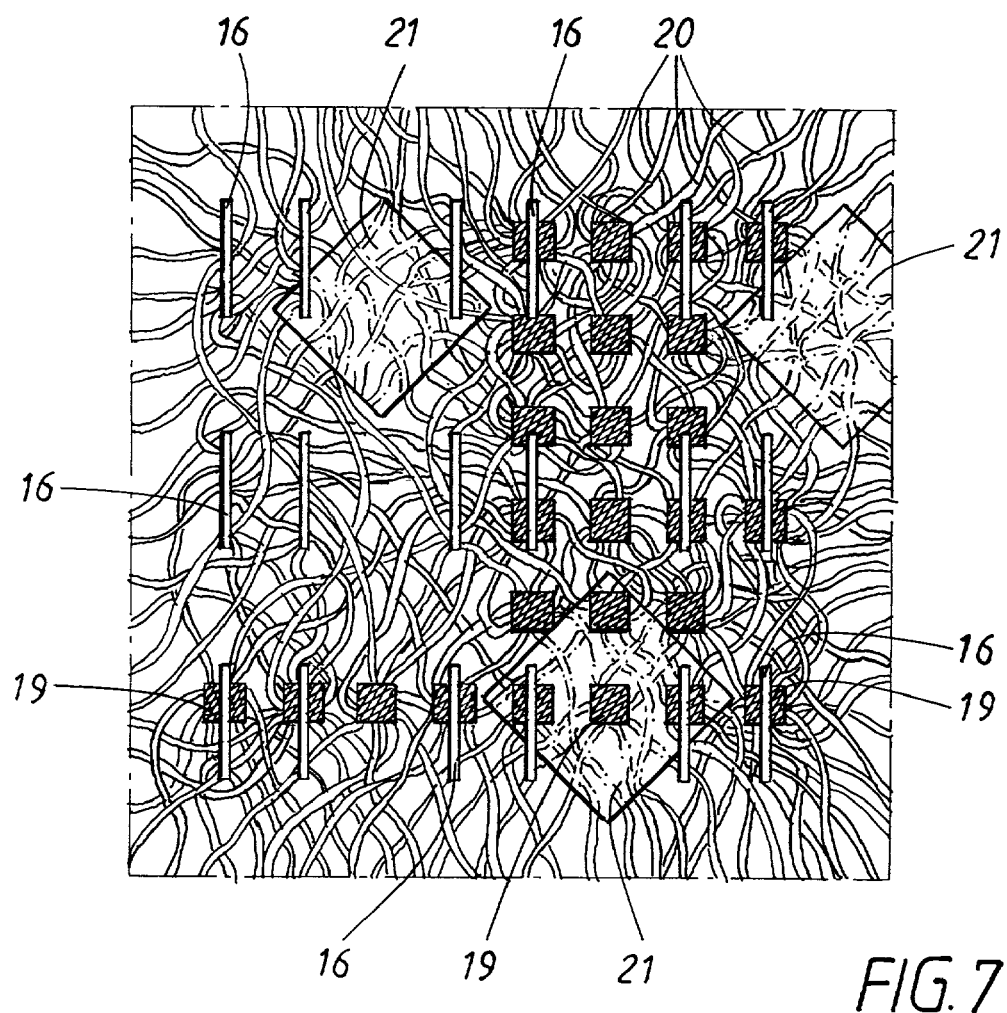
FIG. 7 shows diagrammatically the construction of the laminate according to an embodiment of the invention.

In FIG. 7, which shows diagrammatically a portion of one embodiment of the whole laminate with inner and outer layers, the intention is again to illustrate how the slits 16 through the laminate open it up for forming flow holes but also for softening the material. In FIG. 7, the same reference numbers as in FIG. 6 have been used, reference number 19 indicating thermal bonding points in the bonding pattern of the outer spunbond layer. The slits through the material have been designated by reference number 16 and the spunbond fibers by reference number 20.

According to an embodiment of the invention, the inner layer consists of a carded synthetic wadding, comprising a mixture of PET fibers, PET/copolymer PET bonding fibers and PET/PP fibers. The wadding can be thermally bonded by means of hot air, what is known as through-air bonding. Alternative methods of bonding the wadding are by, but not limited to, needling, thermobonding, bonding using water jets, or bonding agents, such as latex. In these preferred embodiments the two layers are interconnected by means of a first bonding pattern, which consists of separate bonding points. These have been indicated by reference number 21 in FIG. 7. In the illustrative embodiment of the invention shown in FIG. 7, bonding points of square shape have been selected, but other shapes are of course possible, for example rhombic or elongate bonding areas. These bonding points, which have according to one illustrative embodiment been brought about by means of ultrasound, are suitably larger in area than the thermal bonding points 19. As can be seen from FIG. 7, the slits cut through fibers 20 and divide both the bonding points of the spunbond layer and the ultrasonically produced bonds 21 which bond together the two layers making up the laminate.

The size of the bonds 19 and 21 and the number of bonds per unit area in the respective bonding patterns for the outer layer 5 made of spunbond or other non-woven fabric and for the laminate can be varied as required by the intended properties with regard to durability and softness. The size of the slits 16 and the number of slits per unit area can also be varied to control the openness in the laminate and also to control the desired softness.

In an illustrative embodiment of the invention, bonding points of square shape have been selected, but other shapes are of course possible, for example, but not limited to, rhombic or elongate bonding areas. When relatively large bonding points are used, such as the square ones shown, it may be suitable, in conjunction with the ultrasonic bonding, to knurl the square bonding points to form smaller separate parts. This is effected by, for example, dividing each bonding point up into four smaller squares which are separated from one another by elongate areas, the outer plane of which does not coincide with said smaller squares. By knurling, it is possible to avoid large smooth areas being formed at the bonding points. Such large smooth areas could otherwise result in drops of liquid, such as menstrual fluid, adhering to these large areas and not being drawn into the product.

According to another embodiment of the invention, FIG. 8 shows a method of manufacturing a laminate, which has been modified slightly in relation to that according to FIG. 3. The perforating unit in the form of perforating rollers 10, 11, described in connection with FIG. 3 above, has in this case been arranged for perforation of only the spunbond material 5. Lamination of the outer perforated layer 5 and the inner fibrous layer 6 is performed subsequently in the ultrasound unit 9. The laminate 2 in the embodiment according to FIG. 8 is therefore not as open as a laminate which has through-perforations, as described in connection with FIGS. 3-7 above. The open structure of the outer layer in the laminate, which open structure has been brought about by the perforations, the slits, through the spunbond layer results in this embodiment as well in a very soft surface material compared with previously known surface materials for use on absorbent articles.

The laminate according to the invention, is not limited to the illustrative embodiments described above, but a number of modifications are possible within the scope of the patent claims below. For example, the number of holes per unit area can be greater than the number of thermal bonding points 19 per unit area in the spunbond layer, which produces a very soft and open material.

As described above, the outer layer 5 can consist of spunbond. Alternatively, the outer layer can consist of, but is not limited to, carded non-woven fabric. Spunbond and carded non-woven fabric can be bonded by hot air, that is to say what is known as through-air bonding, by needling, by thermo-bonding such as ultrasonic bonding, or means of water jets.

In an illustrative embodiment of the invention shown in FIG. 4, each hole is formed by means of two adjacent parallel slits and by virtue of the material between the slits being pressed down so that hole openings which are essentially at right angles to the plane of the surface material are formed. This results in a very open surface material while obtaining softness by means of the slits. The holes in the outer layer can be made in another way. For example, the holes can consist of slits 16 in a plane outer layer, that is to say the outer layer is not pressed down in the areas between adjacent slits. The holes can also have any other shape. The essential feature in this particular embodiment is that the fibers in the surface material are cut through so as to soften it.

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. A laminate made of fibrous layers for use in absorbent articles, comprising:
    a non-woven fabric outer layer which is in contact with the wearer during use of the article;
    an inner layer connected to the outer layer in a first bonding pattern of multiple interlayer bonding points separate from an edge portion of the outer layer;
    wherein the laminate contains separate holes at least through the outer layer, the holes arranged in a hole pattern; wherein the hole pattern has a density of holes per unit area that is greater than a density of the interlayer bonding points per unit area in the first bonding pattern; and wherein each of said holes comprises two parallel slits delimiting the hole through at least the outer layer, and a depressed rectangular area between the slits.

2. The laminate according to claim 1, wherein the outer layer consists of non-woven fabric with outer layer bonding points arranged in a second bonding pattern, which second bonding pattern has fewer outer layer bonding points per unit area than the number of holes per unit area in said hole pattern.

3. The laminate according to claim 1, wherein the inner layer consists of a non-woven containing at least polyester fibers.

4. The laminate according to claim 3, wherein the inner layer also contains bonding fibers in the form of PET/copolymer PET fibers.

5. The laminate according to claim 1, wherein the outer layer consists of a spunbond made of polypropylene, with a weight per unit area of about 10-40 g/m$^2$.

6. The laminate according to claim 1, wherein the outer and inner layers are thermally bonded to one another at said interlayer bonding points in the first bonding pattern.

7. The laminate according to claim 6, wherein said thermal bonding is brought about by means of ultrasound.

8. The laminate according to claim 1, wherein the outer layer consists of a spunbond made of polypropylene, thermally bonded in a regular second pattern of separate bonding areas with a total bonding area of about 10-25% in addition to which the number of bonding areas in said second bonding pattern is about 10 to 55 per cm$^2$, inclusive.

9. The laminate according to claim 1, wherein the number of interlayer bonding points in the first bonding pattern is less than about 10 per cm$^2$.

10. A laminate made of fibrous layers for use in absorbent articles, comprising:
    a non-woven fabric outer layer which is in contact with the wearer during use of the article; and
    an inner layer connected to the outer layer in a first bonding pattern of multiple interlayer bonding points;
    wherein the inner layer consists of a carded synthetic wadding, comprising a mixture of PET fibers, PET/copolymer PET bonding fibers and PET/PP fibers, which wadding is bonded by means of hot air;
    wherein the laminate contains separate holes at least through the outer layer, the holes arranged in a hole pattern; the hole pattern having a density of holes per unit area that is greater than a density of the interlayer bonding points per unit area in the first bonding pattern; and
    wherein each of said holes includes at least one slit through at least the outer layer.

11. The laminate according to claim 1, wherein the inner layer has a weight per unit area of about 30-70 g/m$^2$.

12. The laminate according to claim 1, wherein the outer layer consists of a spunbond made of polypropylene, with a weight per unit area of about 20-25 g/m$^2$.

13. The laminate according to claim 1, wherein the outer layer consists of a spunbond made of polypropylene, thermally bonded in a regular second pattern of separate bonding areas with a total bonding area of about 10-15% in addition to which the number of bonding areas in said second bonding pattern is about 10 to 55 per cm$^2$.

14. The laminate according to claim 1, wherein the outer layer consists of a spunbond made of polypropylene, thermally bonded in a regular second pattern of separate bonding areas with a total bonding area of about 10-25% in addition to which the number of bonding areas in said second bonding pattern is about 30 to 35 per cm$^2$.

15. The laminate according to claim 1, wherein the outer layer consists of a spunbond made of polypropylene, thermally bonded in a regular second pattern of separate bonding areas with a total bonding area of about 10-15% in addition to which the number of bonding areas in said second bonding pattern is about 30 to 35 per cm$^2$.

16. A laminate made of fibrous layers for use in absorbent articles, the laminate comprising:
- a non-woven fabric outer layer which is in contact with the wearer during use of the article;
- an inner layer connected to the outer layer in a first bonding pattern of multiple interlayer bonding points separate from an edge portion of the outer layer;
- the laminate containing separate holes at least through the outer layer, the holes arranged in a hole pattern;
- the hole pattern having a density of holes per unit area that is greater than a density of the interlayer bonding points per unit area in the first bonding pattern; and
- wherein each of said holes includes at least one slit through at least the outer layer and an area adjacent the at least one slit is at a lower level than a remaining portion of the outer layer.

17. The laminate according to claim 16, wherein each hole includes a second slit parallel to the at least one slit and the area that is at a lower level is between the at least one slit and the second slit.

18. The laminate according to claim 16, wherein area adjacent the slit at a lower level than the remaining portion of the outer layer is depressed from the outer layer by having been pressed down.

* * * * *